(12) United States Patent
Liphardt et al.

(10) Patent No.: US 7,671,989 B2
(45) Date of Patent: Mar. 2, 2010

(54) INFORMATION MAINTENANCE DURING INTENSITY ATTENUATION IN FOCUSED BEAMS

(75) Inventors: Martin M. Liphardt, Lincoln, NE (US); Ping He, Lincoln, NE (US)

(73) Assignee: J. A. Woollam Co., Inc., Lincoln, NE (US)

( * ) Notice: Subject to any disclaimer, the term of this patent is extended or adjusted under 35 U.S.C. 154(b) by 135 days.

(21) Appl. No.: 12/214,319

(22) Filed: Jun. 18, 2008

(65) Prior Publication Data

US 2008/0285035 A1 Nov. 20, 2008

Related U.S. Application Data

(63) Continuation-in-part of application No. 11/648,060, filed on Dec. 29, 2006, now Pat. No. 7,554,662, and a continuation-in-part of application No. 11/204,929, filed on Aug. 15, 2005, now Pat. No. 7,468,794, and a continuation-in-part of application No. 10/178,723, filed on Jun. 24, 2002, now Pat. No. 6,950,182, and a continuation-in-part of application No. 10/699,540, filed on Nov. 1, 2003, now Pat. No. 7,158,231.

(60) Provisional application No. 60/936,141, filed on Jun. 19, 2007.

(51) Int. Cl.
*G01J 4/00* (2006.01)

(52) U.S. Cl. .................. 356/369; 356/370; 359/238; 359/894

(58) Field of Classification Search .......... 356/364–370; 359/238, 251, 290, 894
See application file for complete search history.

(56) References Cited

U.S. PATENT DOCUMENTS

| 3,905,675 | A | 9/1975 | McCracher | 350/17 |
|---|---|---|---|---|
| 4,053,232 | A | 10/1977 | Dill et al. | 356/369 |
| 4,877,960 | A | 10/1989 | Messerschmult et al. | 250/341 |
| 4,996,120 | A | 2/1991 | Smothers et al. | 430/2 |
| 5,032,734 | A | 7/1991 | Orazio, Jr. et al. | 250/572 |
| 5,042,951 | A | 8/1991 | Gold | 356/369 |
| 5,148,323 | A | 9/1992 | Campbell et al. | 359/738 |
| 5,159,412 | A | 10/1992 | Willenborg et al. | 356/445 |
| 5,166,752 | A | 11/1992 | Spanier | 356/369 |
| 5,329,357 | A | 7/1994 | Bernoux et al. | 356/369 |
| 5,373,359 | A | 12/1994 | Woollam et al. | 356/328 |
| 5,414,559 | A | 5/1995 | Burghardt et al. | 359/623 |
| 5,426,506 | A | 6/1995 | Ellingson et al. | 356/369 |
| 5,504,582 | A | 4/1996 | Johs et al. | 356/369 |
| 5,517,312 | A | 5/1996 | Finarov | 356/386 |
| 5,521,706 | A | 5/1996 | Green et al. | 356/369 |
| 5,608,526 | A | 3/1997 | Piwonka-Corle et al. | 356/369 |
| 5,666,201 | A | 9/1997 | Johs et al. | 356/369 |
| 5,684,642 | A | 11/1997 | Zumoto et al. | 359/740 |
| 5,796,521 | A | 8/1998 | Kahlert et al. | 359/619 |
| 5,805,285 | A * | 9/1998 | Johs et al. | 356/369 |
| 5,859,424 | A | 1/1999 | Norton et al. | 250/226 |
| 5,872,630 | A | 2/1999 | Johs et al. | 356/369 |
| 5,877,859 | A | 3/1999 | Aspnes | 356/364 |
| 5,889,593 | A | 3/1999 | Bareket | 356/445 |
| 5,910,842 | A | 6/1999 | Piwonka-Corle et al. | 356/369 |

(Continued)

*Primary Examiner*—L. G Lauchman
(74) *Attorney, Agent, or Firm*—James D. Welch

(57) ABSTRACT

Maintenance of information content in a focused beam of electromagnetic radiation when the intensity thereof is attenuated by application of an aperture-like element.

7 Claims, 4 Drawing Sheets

U.S. PATENT DOCUMENTS

| | | | |
|---|---|---|---|
| 5,917,594 A | 6/1999 | Norton | 356/327 |
| 5,963,327 A | 10/1999 | He et al. | 356/369 |
| 6,134,012 A * | 10/2000 | Aspnes et al. | 356/369 |
| 6,184,984 B1 | 2/2001 | Lee et al. | 356/369 |
| 6,321,601 B1 | 11/2001 | Maris | 73/65.7 |
| 6,690,473 B1 | 2/2004 | Stanke et al. | 356/601 |
| 6,734,967 B1 | 5/2004 | Piwonka-Corle et al. | 356/369 |
| 7,145,654 B2 | 12/2006 | Norton | 356/369 |

* cited by examiner

BEAM CROSS SECTION

PARAMETER P
(e.g. AOI)

BEAM ATTENUATOR

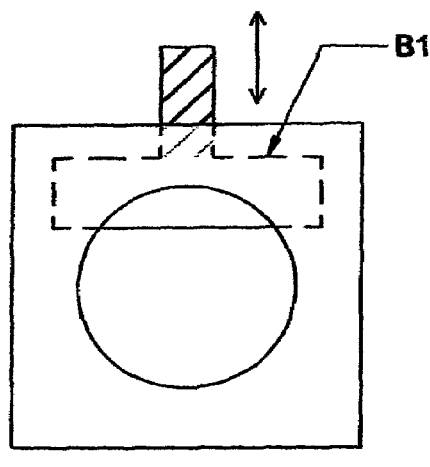
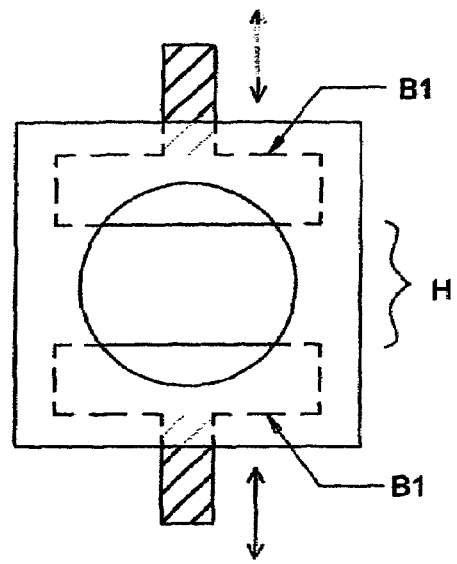
FIG. 3a  FIG. 3b
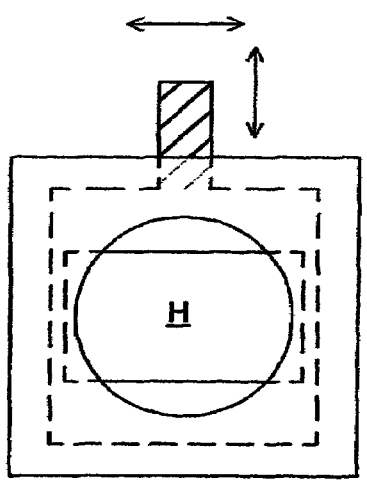
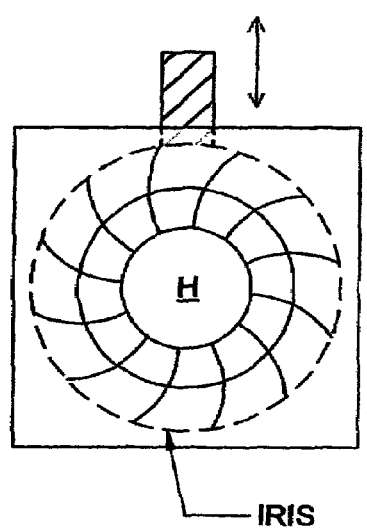
FIG. 3c  FIG. 3d

INFORMATION MAINTENANCE DURING INTENSITY ATTENUATION IN FOCUSED BEAMS

CROSS-REFERENCE TO OTHER APPLICATIONS

This Application Claims benefit of Provisional Application Ser. No. 60/936,141 Filed Jun. 19, 2007. This Application is also a CIP of application Ser. No. 11/648,060 Filed Dec. 29, 2006 now U.S. Pat. No. 7,554,662; and therevia of application Ser. No. 11/204,929 Filed Aug. 15, 2005 now U.S. Pat. No. 7,468,794; and therevia is a CIP of application Ser. No. 10/178,723 Filed Jun. 24, 2002, (now U.S. Pat. No. 6,950,182); and is also a CIP from application Ser. No. 10/699,540 Filed Nov. 1, 2003 (now U.S. Pat. No. 7,158,231).

TECHNICAL AREA

The present invention relates to focused electromagnetic beams, and more particularly to the maintenance of information content therein when the intensity thereof is attenuated by application of an aperture-like element.

BACKGROUND

It is known to attenuated the intensity of electromagnetic beams by applying an aperture or the like in the path thereof when a detector of the beam becomes saturated. This is a straight forward practice where a beam is collimated. However, where a beam is focused, and is caused to impinge on a sample at an oblique angle of incidence, the practice becomes more complicated. This is because a focused beam arrives at a sample at range of angles-of-incidence (AOI), with components passing through a focusing element centrally being at a nominal (AOI) and components thereof which pass through the focusing element laterally being at greater or lesser (AOI's).

Applying an aperture to attenuate beam intensity in such a focused beam situation requires that the aperture be positioned so as to preserve the central component, and substantially equal amounts of the greater and lesser (AOI's) to maintain data affecting characteristics in the attenuated beam similar to those in the unattenuated beam.

It is disclosed that the use of aperture elements in reflectometers and ellipsometers and the like is well known in the art. For instance, a Patent to Liphardt et al., U.S. Pat. No. 7,336,361 discloses an ellipsometer system, in FIG. 1b thereof, with five apertures in the pathway of an electromagnetic beam. Pending Application, Ser. No. 11/648,060 Filed Dec. 29, 2006 from which this Application continues, provides, in FIG. 1a7 thereof, a relevant additional Aperture (NAP) prior to a Detector (DET). Said Parent Applications variously show use of a beam of electromagnetic radiation onto a sample, as is the case in the present invention.

Representative Patents which disclose Apertures in an ellipsometer or the like, provided a Patent to Norton, U.S. Pat. No. 7,145,654. The system therein is described as utilizing a beam focused onto the end of an optical fiber, such that the angular range of the probe beam is less than a natural numerical aperture of an optical fiber. The purpose of the Norton invention is to selectively attenuate and reduce the presence of secondary maxima falling outside a measurement spot on a sample. Minimizing said secondary maxima can improve the amount of light measured by a detector that is reflected from inside a measurement spot. Said 654 Patent is included herein by reference.

A Patent, U.S. Pat. No. 5,517,312 to Finarov describes application of a scattered light reducing system at the entry to a Detector in a Rotating Analyzer or Rotating Polarizer Ellipsometer System, which scattered light reducing system consists of two lenses with a hole containing diaphram located midway therebetween, and at the focal lengths of said lenses. Said scattered light reducing system is present after a sample system and processes electromagnetic radiation after it interacts with said sample system. The pin-hole is described as serving to reduce scattered light and providing high spatial resolution.

Another Patent identified is that to Campbell et al., U.S. Pat. No. 5,148,323. Said 323 Patent describes a Spatial Filter in which a pinhole is located other than at the focal length of a converging lens.

U.S. Pat. No. 3,905,675 to McCraken describes a Spatial Filter containing system which enables observation of a weak source of electromagnetic radiation in the presence of strong sources thereof.

U.S. Pat. No. 5,684,642 to Zumoto et al., describes an optical transmission system for use in fashioning an electromagnetic beam for use in machining materials which combines a Spatial Filter and an Optical Fiber.

U.S. Pat. No. 4,877,960 to Messerschmidt et al. is identified as it describes-masking energy from outside the target area in a microscope having dual remote image masking.

A Patent, U.S. Pat. No. 5,329,357 to Bernoux et al. is identified as it Claims use of fiber optics to carry electromagnetic radiation to and from an ellipsometer system which has at least one polarizer or analyzer which rotates during data acquisition. It is noted that if both the polarizer and analyzer are stationary during data acquisition that this Patent is not controlling where electromagnetic radiation carrying fiber optics are present.

Continuing, Spectroscopic Ellipsometer Systems are also known in the art. Application a Spatial Filters near a Detector, in the context of Rotating Polarizer and Rotating Analyzer Ellipsometer Systems has been reported, (see U.S. Pat. No. 5,517,312 to Finerov). It is noted, that application of Spatial Filters in Rotating Compensator Ellipsometer Systems, such as the Rotating Compensator Ellipsometer System Claimed in co-owned U.S. Pat. No. 5,872,630, has been described in Co-Pending application Ser. No. 11/204,929 by the inventors herein. Said 630 Patent and 929 Application, are incorporated by reference hereinto and are co-owned with this Application.

For general reference, a Patent to Dill et al., U.S. Pat. No. 4,053,232 is disclosed as it describes a Rotating-Compensator Ellipsometer System which operates utilizing monochromatic light. Further, a Patent to Aspnes et al., U.S. Pat. No. 5,877,859 is disclosed as it describes a Broadband Spectroscopic Rotating Compensator Ellipsometer System wherein the Utility is derived from selecting a wavelength range and compensator so that at least one wavelength in said wavelength range has a retardation imposed of between 135 and 225 degrees, and another wavelength in said wavelength range has a retardation imposed which is outside that retardation range. Further Patents of general interest of which the Inventors are aware include those to Woollam et al, U.S. Pat. No. 5,373,359, Patent to Johs et al. U.S. Pat. No. 5,666,201 and Patent to Green et al., U.S. Pat. No. 5,521,706, and Patent to Johs et al., U.S. Pat. No. 5,504,582 are disclosed for general information as they pertain to ellipsometer systems. A Patent to He et al., U.S. Pat. No. 5,963,327 is also disclosed as it describes a laterally compact ellipsometer system which enables providing a focused polarized beam of electromagnetic radiation at an oblique angle-of-incidence to a sample system in a small spot area.

Patents to Piwonka-Corle, U.S. Pat. Nos. 5,608,526, 5,910,842 and 6,734,967 describe focused beam spectroscopic ellipsometer systems which include means for selecting ranges of angles of incidence reflecting from a sample. Additionally, Patents to Gold, U.S. Pat. No. 5,042,951 and Spanier, U.S. Pat. No. 5,166,752 are disclosed for a similar reason. The present invention differs as no specific guidance as to how to select a range of wavelengths around a nominal angle of incidence to preserve information in a reflected and monitored beam is taught in said Patents.

It is also of interest to note that a computer search for Patents which include both the terms "focused beam" and "aperture" provided only two Patents, namely, U.S. Pat. Nos. 5,159,412 to Willenborg et al. and 6,690,473 to Stanke et al., neither of which is particularly relevant to the present invention. Further, U.S. Pat. Nos. 5,910,842, 6,734,967 to Pivonka-Corle et al. are disclosed as they describe use of focused beams in ellipsometry.

Even in view of the known art, need remains for a system and method of its use which enables maintenance of information content in a focused beam of electromagentic radiation when he intensity thereof is attenuated by application of an aperture-like element.

DISCLOSURE OF THE INVENTION

The present invention is a system for providing intensity attenuation to a focused beam of electromagnetic radiation, the locus thereof being oriented to provide a plurality of oblique angles-of-incidence to a sample, some greater and some lesser than an average angle-of-incidence value, while maintaining information therein.

Said system can be a reflectometer comprising a source of a beam of electromagnetic radiation and a detector system sequentially positioned such that said source provides a collimated beam of electromagnetic radiation which is caused to become said focused beam, and reflect from said sample before passing through a collimating means and proceeding to said detector system.

Said system can also be an ellipsometer comprising a means for blocking substantially equally amounts of greater and lesser than an average angles-of-incidence beam components such that an average angle-of-incidence for both the unattenuated and attenuated beams are equal. Said system typically comprises a source of a beam of electromagnetic radiation, a polarization state generator, a polarization state analyzer and a detector systems sequentially positioned such that said source provides a collimated beam of electromagnetic radiation which is directed to pass through said a polarization state generator, then become said focused beam and reflects from said sample before passing through a collimating means and said polarization state analyzer and proceeding to said detector system. Said system can further comprise said detector system comprising a beam splitter and two detectors positioned such that said beam proceeding to said detector system partially reflects from said beam splitter and enters the first detector, and partially passes through said beam splitter and enters said second detector. There can further be a mirror between said beam splitter and said second detector.

A present invention method of attenuating the intensity of a focused beam of electromagnetic radiation, the locus of which is oriented to provide a plurality of oblique angles-of-incidence to a sample, said attenuation being entered while maintaining information in a beam reflected from said sample, comprises the steps of:

a) providing a system for providing intensity attenuation to a focused beam of electromagnetic radiation, the locus of which is oriented to provide a plurality of oblique angles-of-incidence to a sample, some greater and some lesser than an average angles-of-incidence value, while maintaining information therein, comprising a means for blocking substantially equally amounts of greater and lesser than an average angles-of-incidence beam components such that an average angle-of-incidence for both the unattenuated and attenuated beams are equal;

b) determining a need to attenuate the intensity of said beam;

c) entering an attenuation element into the path of said beam such that substantially equal amounts of beam components with greater than average angle-of-incidence and with lesser than average angle-of-incidence are blocked;

such that both before and-after entry of said attenuation element the average angle-of-incidence is substantially the same value.

Another method of attenuating the intensity of a focused beam of electromagnetic radiation, the locus of which is oriented to provide a plurality of oblique angles-of-incidence to a sample, said attenuation being entered while maintaining information in a beam reflected from said sample, comprises the steps of:

a) providing a system for providing intensity attenuation to a focused beam of electromagnetic radiation, the locus of which is oriented to provide a plurality of oblique angles-of-incidence to a sample, some greater and some lesser than an average angles-of-incidence value, while maintaining information therein; said system comprising a source of a beam of electromagnetic radiation, a polarization state generator, a polarization state analyzer and a detector system sequentially positioned such that said source provides a collimated beam of electromagnetic radiation which is directed to pass through said a polarization state generator, then become said focused beam and reflect from said sample before passing through a collimating means and said polarization state analyzer and then proceeding to said detector system; wherein said detector system comprises a beam splitter and two detectors positioned such that said beam proceeding to said detector system partially reflects from said beam splitter and enters the first detector, and partially passes through said beam splitter and enters said second detector, said first and second detectors being appropriate to detect adjacent ranges of wavelengths;

said system further comprising means for blocking substantially equally amounts of beam components corresponding to greater than and lesser than an average angles-of-incidence beam components such that an average angle-of-incidence for both the unattenuated and attenuated beams are equal, at least at one location selected from the group consisting of:

located to intercept the beam entering said beam splitter;

located to intercept the beam entering said first detector; and located to intercept the beam entering said second detector;

b) determining a need to attenuate the intensity of said beam;

c) applying at least one said selected means for blocking substantially equally amounts of greater and lesser than an average angles-of-incidence beam components to block substantially equal amounts of beam components with greater than average angle-of-incidence and with lesser than average angle-of-incidence are blocked;

such that data obtained at abutting wavelengths by said two detectors in said two ranges are continuous, or such that in an overlap of wavelengths region wherein both detectors provide data therefore, both detectors provide the same reading.

It is noted that while in a practical sense it would be substantially unavoidable, in the foregoing method it is not absolutely required that there be at least one wavelength of overlap of the two detectors, and in such a case it is required that there be a continuous plot at abutting wavelengths.

In view of the foregoing it is to be understood that a system for accomplishing the desired result can be assembled and calibrated using a relatively low reflectivity sample, so that data can be obtained both before and after application of an Information Maintaining Attenuator, (eg. aperture-like element). Further, a table of data can be assembled during the calibration procedure that allows one to set a desired amount of attenuation without having to again practice the calibration process.

Finally, the whole process can be automated so that a saturated detector provides a signal to effect information maintaining attenuation, and then, with said attenuating entered in a way that preserves the average angle-of-incidence, proceed to acquire data.

The present invention will be better understood by reference to the Detailed Description Section of this Specification.

BRIEF DESCRIPTION OF THE DRAWINGS

FIG. 2a1 shows a beam cross-section of an unattenuated beam.

FIG. 2a2 shows a plot of a parameter, (eg. AOI), of the beam in FIG. 2a1.

FIG. 2b1 shows a beam cross-section of an attenuated beam.

FIG. 2b2 shows a plot of a parameter, (eg. AOI), of the beam in FIG. 2b1.

FIGS. 3a-3d show various embodiments of beam attenuation elements.

DETAILED DESCRIPTION

Figure 1:
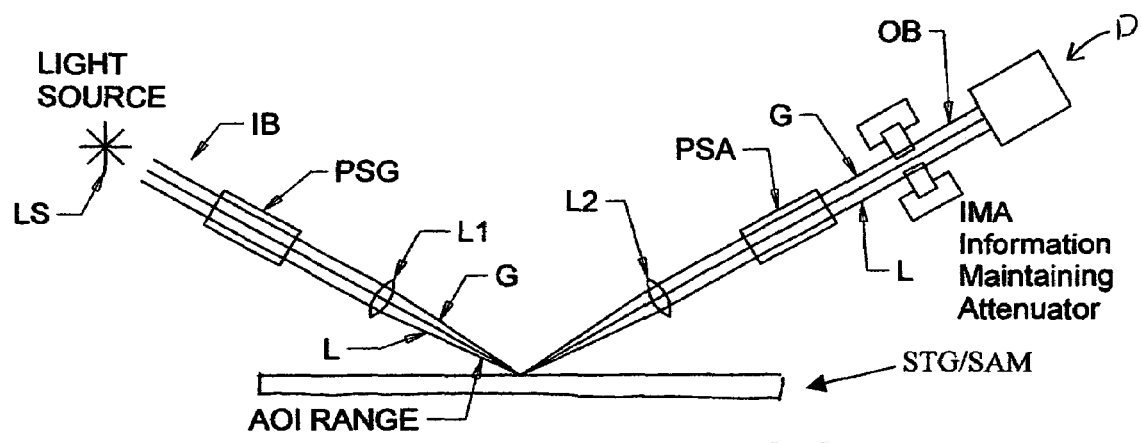
FIG. 1 shows an ellipsometer system with a focused electromagnetic beam.

Turning now to the Drawings, FIG. 1 shows a demonstrative ellipsometer system using a focused electromagnetic beam. Shown are a Source (LS) of a beam of electromagnetic radiation, a Polarization State Generator (PSG), a First Focusing Means (L1), a Stage and Sample (STG/SAM), a Collimation Means (L2), a Polarization State Analyzer (PSA) and a Detector (DET). The system also comprises an Information Maintaining Attenuator (IMA).

In use the beam of electromagnetic radiation passing through the Information Maintaining Attenuator (IMA) and into the Detector (DET) might be of too high an intensity and saturate the Detector electronics. This might happen where a Sample is very reflective, for instance. In such as case the (IMA) can be operated to block some of the Output Beam (OB). This might be accomplished by, for instance, placing a smaller opening aperture in place, or operating an iris. Importantly, it is specifically noted that the focused beam (IB) has components with Greater (G) and Lesser (L) (AOI's).

It is noted that if the Polarization State Generator (PSG) and Polarization State Analyzer (PSA) are removed from FIG. 1, the result is a Reflectometer.

Figure 2A:
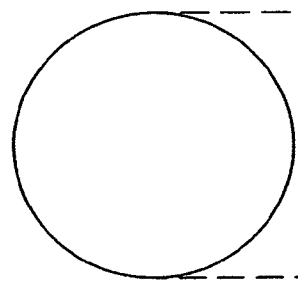
Figure 2A:
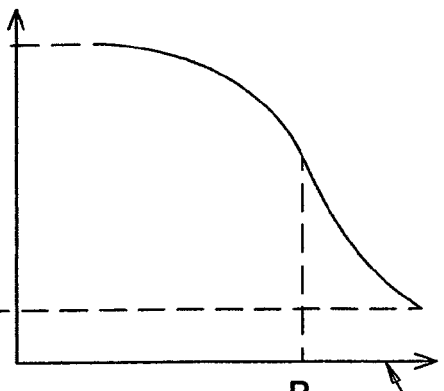
Figure 2B:
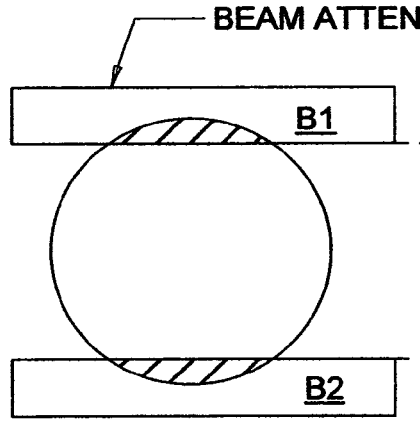
Figure 2B:
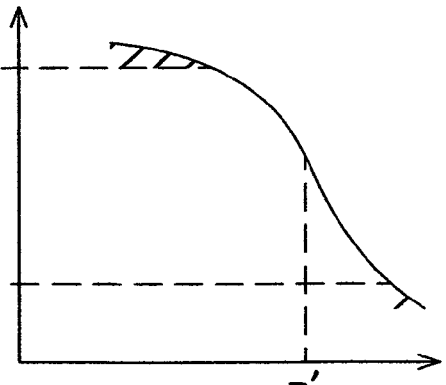

Continuing, FIG. 2a1 shows a beam cross-section of an unattenuated beam and FIG. 2a2 shows a plot of a parameter, (eg. AOI), of the beam in FIG. 2a1. Note in particular that an average location (Peff) is indicated. Now, FIG. 2b1 shows a beam cross-section of an attenuated beam and FIG. 2b2 shows a plot of a parameter, (eg. AOI), of the beam in FIG. 2b1. Note again that there is an associated average location (Peff'). If the (IMA) is symetrically applied to equally block Greater (G) and Lesser (L) (AOI) components then (Peff) and (Peff') will be equal. This point is-at the heart of the present invention.

Figure 4:
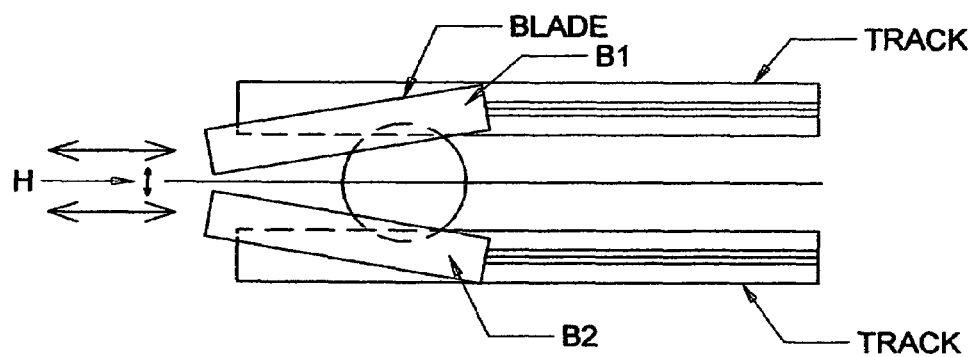
FIG. 4 shows a knife-edge system for controlling beam attenuation.

FIGS. 3a-3d show various embodiments of beam attenuation elements. FIG. 3a shows a single sided Beam Blocking element (B1), and FIG. 3b shows a double Beam Blocking element system (B1) (B2). FIG. 3c shows a rectangular shaped opening (H) in a single Beam Blocking element, which rectangular shaped (H) opening can be moved with respect to the Beam cross-section. FIG. 3d shows an Iris Beam Blocking element with a circular (H). FIG. 4 shows a dual knife-edge system for controlling beam attenuation from the top and bottom of a beam. Note an effective Hole (H) is formed by the edges of the two Blades (B1) (B2).

Figure 5:
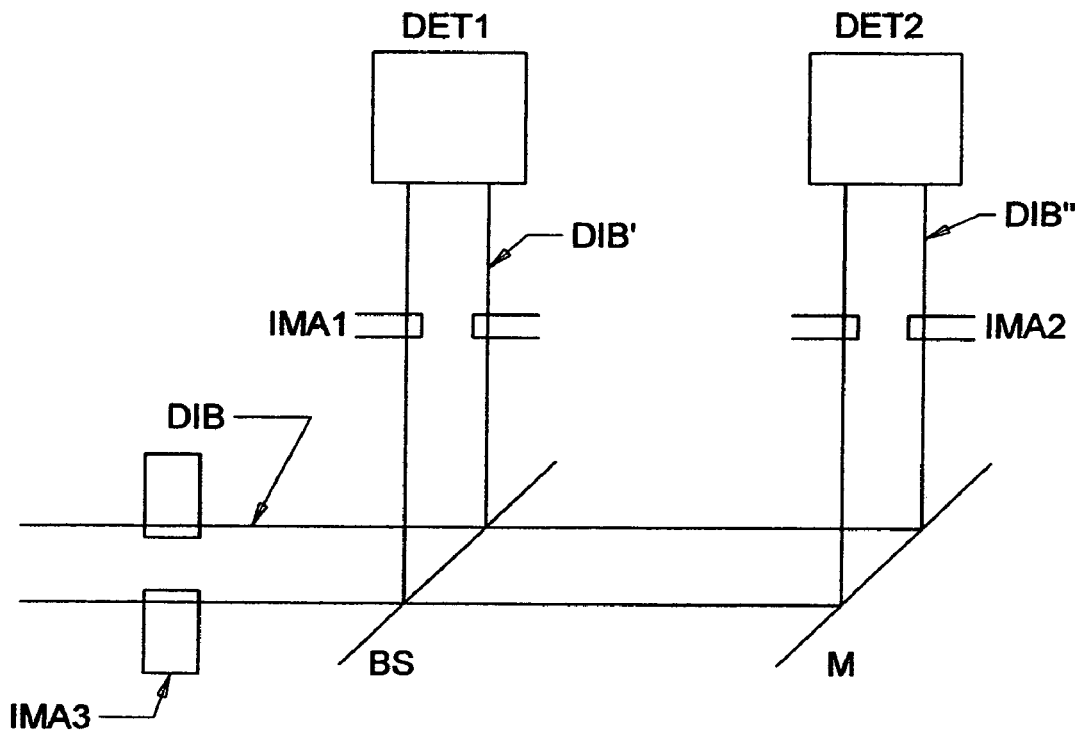
FIG. 5 shows a multiple detector system wherein different ranges of wavelengths are caused to enter different detectors, including intensity attenuation elements.
Figure 6:
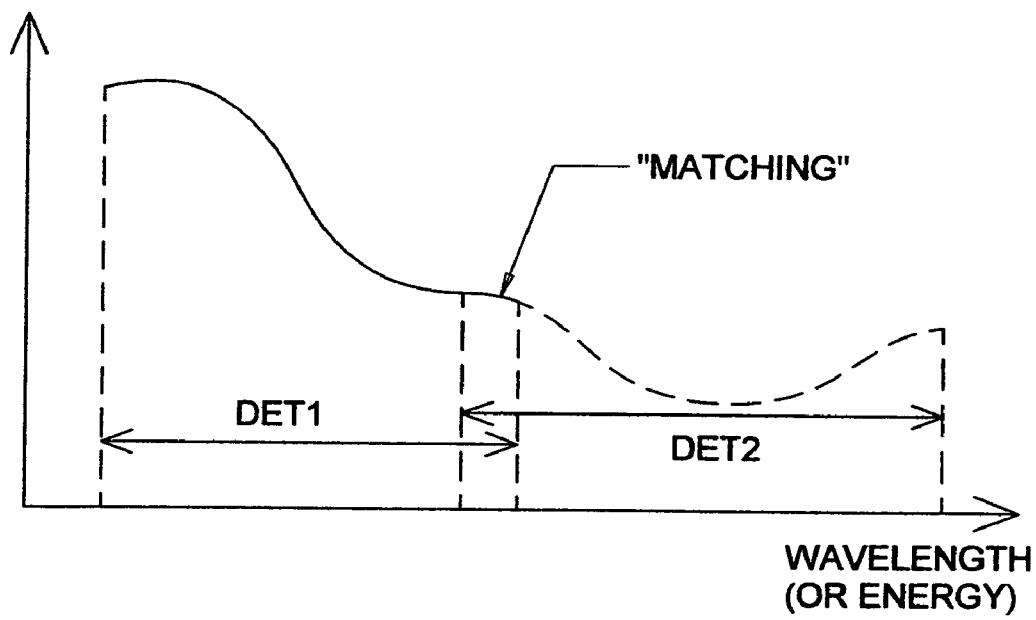
FIG. 6 shows a plot of data obtained from a system as in FIG. 5, showing that where attenuation is properly applied data in an overlap range of wavelengths matches.

FIG. 5 shows a multiple detector system wherein different ranges of wavelengths are caused to enter different detectors, including intensity attenuation elements. Shown are a Detector Input Beam (DIB) which passes through Information Maintaining Attenuator (IMA3) before being partially passed and partially reflected by Beam Splitter (BS). The reflected part of (DIB) enters the First Detector (DET1) via Information Maintaining Attenuator (IMA1) and the transmitted part of (DIB) enters the Second Detector (DETs) via Information Maintaining Attenuator (IMA2) after reflection from Mirror (M). FIG. 6 shows that if Attenuation providing means are properly adjusted, a plot of some Parameter, (eg. Intensity), vs. Wavelength obtained partially from Detector (DET1) and partially from Detector (DET2) will provide the same data where the Wavelengths monitored overlap.

Finally, it is noted that while the disclosure-used angle-of-incidence as an example, planes-of-incidence can also be adjusted likewise so that equal amounts of greater and lesser than an average plane-of-incidence beam components are blocked, such that an average plane-of-incidence for both the unattenuated and attenuated beams are equal. The Claims should be read to cover the angle of incidence, and optionally the plane of incidence.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A system for providing intensity attenuation to a recollimated focused beam of electromagnetic radiation, the locus of which focused beam is oriented to provide a plurality of oblique angles-of-incidence to a sample, some greater and some lesser than an average angle-of-incidence value, while maintaining information therein, said system comprising a means for blocking substantially equal amounts of greater and lesser than an average angle-of-incidence beam component in the recollimated focused beam, such that an average angle-of-incidence for both the unattenuated and attenuated beams are equal.

2. A system as in claim 1 which further comprises a source of a beam of electromagnetic radiation and a detector system sequentially positioned such that said source provides a collimated beam of electromagnetic radiation which is caused to become said focused beam, and reflect from said sample before passing through a collimating means and proceeding to said detector system;

where said system is a reflectometer.

3. A system as in claim 1 which further comprises a source of a beam of electromagnetic radiation, a polarization state generator, a polarization state analyzer and a detector system sequentially positioned such that said source provides a collimated beam of electromagnetic radiation which is directed to pass through said a polarization state generator, then become said focused beam and reflects from said sample before passing through a collimating means and said polarization state analyzer and proceeding to said detector system;

where said system is an ellipsometer.

4. A system as in claim 3, wherein said detector comprises a beam splitter and two detectors positioned such that said beam proceeding to said detector system partially reflects from said beam splitter and enters the first detector, and partially passes through said beam splitter and enters said second detector.

5. A system as in claim 4 which further comprises a mirror between said beam splitter and said second detector.

6. A method of attenuating the intensity of a beam of electromagnetic radiation, the locus of which is oriented to provide a plurality of oblique angles-of-incidence to a sample, said attenuation being entered while maintaining information in a beam reflected from said sample, comprising the steps of:
   a) providing a system for providing intensity attenuation to a recollimated focused beam of electromagnetic radiation, the locus of which focused beam is oriented to provide a plurality of oblique angles-of-incidence to a sample, some greater and some lesser than an average angles-of-incidence value, while maintaining information therein, said system comprising a means for blocking substantially equal amounts of greater and lesser than an average angle-of-incidence beam component in the recollimated focused beam, such that an average angle-of-incidence for both the unattenuated and attenuated beams are equal;
   b) determining a need to attenuate the intensity of said recollimated focused beam;
   c) entering an attenuation element into the path of said recollimated focused beam such that substantially equal amounts of beam components with greater than average angle-of-incidence and with lesser than average angle-of-incidence are blocked;
such that both before and after entry of said attenuation element the average angle-of-incidence is substantially the same value.

7. A method of attenuating the intensity of a recollimated focused beam of electromagnetic radiation, the locus of which focused beam is oriented to provide a plurality of oblique angles-of-incidence to a sample, said attenuation being entered while maintaining information in a beam reflected from said sample, said method comprising the steps of:
   a) providing a system for providing intensity attenuation to a recollimated focused beam of electromagnetic radiation, the locus of which focused beam is oriented to provide a plurality of oblique angles-of-incidence to a sample, some greater and some lesser than an average angles-of-incidence value, while maintaining information therein; said system comprising a source of a beam of electromagnetic radiation, a polarization state generator, a polarization state analyzer and a detector system sequentially positioned such that said source provides a collimated beam of electromagnetic radiation which is directed to pass through said a polarization state generator, then become said focused beam and reflect from said sample before passing through a collimating means and said polarization state analyzer and then proceeding to said detector system; wherein said detector system comprises a beam splitter and two detectors positioned such that said recollimated focused beam proceeding to said detector system partially reflects from said beam splitter and enters the first detector, and partially passes through said beam splitter and enters said second detector, said first and second detectors being appropriate to detect adjacent ranges of wavelengths;
   said system further comprising means for blocking substantially equal amounts of beam components in the recollimated focused beam, which corresponding to greater than and lesser than an average angle-of-incidence beam component in the recollimated focused beam, such that an average angle-of-incidence for both the unattenuated and attenuated beams are equal, said system being present at least at one location selected from the group consisting of:
   located to intercept the recollimated focused beam entering said beam splitter;
   located to intercept the recollimated focused beam entering said first detector; and
   located to intercept the recollimated focused beam entering said second detector;
   b) determining a need to attenuate the intensity of said recollimated focused beam;
   c) applying at least one said selected means for blocking substantially equal amounts of beam components in the recollimated focused beam which correspond to greater and lesser than an average angle-of-incidence of the focused beam component to block substantially equal amounts of beam components with greater than average angle-of-incidence and with lesser than average angle-of-incidence;
such that data obtained at abutting wavelengths by said two detectors in said two wavelength ranges are continuous, or such that in an overlap of wavelengths region wherein both detectors provide data therefore, both detectors provide the same reading.

* * * * *